United States Patent
Toyoshima et al.

(10) Patent No.: US 9,285,383 B2
(45) Date of Patent: Mar. 15, 2016

(54) SPECIMEN ANALYZER

(71) Applicants: Hiroto Toyoshima, Kobe (JP); Kouichi Masutani, Kobe (JP)

(72) Inventors: Hiroto Toyoshima, Kobe (JP); Kouichi Masutani, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 100 days.

(21) Appl. No.: 14/024,187

(22) Filed: Sep. 11, 2013

(65) Prior Publication Data

US 2014/0079591 A1 Mar. 20, 2014

(30) Foreign Application Priority Data

Sep. 20, 2012 (JP) ................. 2012-207500

(51) Int. Cl.
*G01N 35/04* (2006.01)
*G01N 35/10* (2006.01)

(52) U.S. Cl.
CPC ........ *G01N 35/04* (2013.01); *G01N 2035/0406* (2013.01); *G01N 2035/0465* (2013.01); *G01N 2035/103* (2013.01)

(58) Field of Classification Search
None
See application file for complete search history.

(56) References Cited

U.S. PATENT DOCUMENTS

| | | | | |
|---|---|---|---|---|
| 4,519,507 A * | 5/1985 | Gillette et al. | ................ | 209/682 |
| 4,576,286 A * | 3/1986 | Buckley et al. | ............... | 209/558 |
| 4,923,067 A * | 5/1990 | Fuller et al. | ................... | 209/539 |
| 6,986,439 B2 * | 1/2006 | Itoh | ............................. | 221/167 |
| 2003/0047418 A1 * | 3/2003 | Okada et al. | ............... | 198/459.1 |
| 2004/0131499 A1 * | 7/2004 | Okada et al. | .................... | 422/64 |
| 2007/0212260 A1 * | 9/2007 | Fukuda et al. | .................. | 422/64 |
| 2011/0086432 A1 | 4/2011 | Herz et al. | | |
| 2012/0195798 A1 * | 8/2012 | Kowari et al. | ................... | 422/69 |

FOREIGN PATENT DOCUMENTS

| | | |
|---|---|---|
| CN | 102621337 A | 8/2012 |
| JP | 2003-083999 A | 3/2003 |

* cited by examiner

*Primary Examiner* — Jill Warden
*Assistant Examiner* — Benjamin Whatley
(74) *Attorney, Agent, or Firm* — Sughrue Mion, PLLC

(57) ABSTRACT

A specimen analyzer comprises a measurement mechanism section configured to measure a specimen by using a first consumable and a second consumable having a shape different from a shape of the first consumable, a first inlet for loading the first consumable, a supplying section configured to supply the first consumable loaded through the first inlet, to the measurement mechanism section, a sorter configured to sort the first consumable and the second consumable from each other, and a storage for housing the second consumable sorted by the sorter.

12 Claims, 13 Drawing Sheets

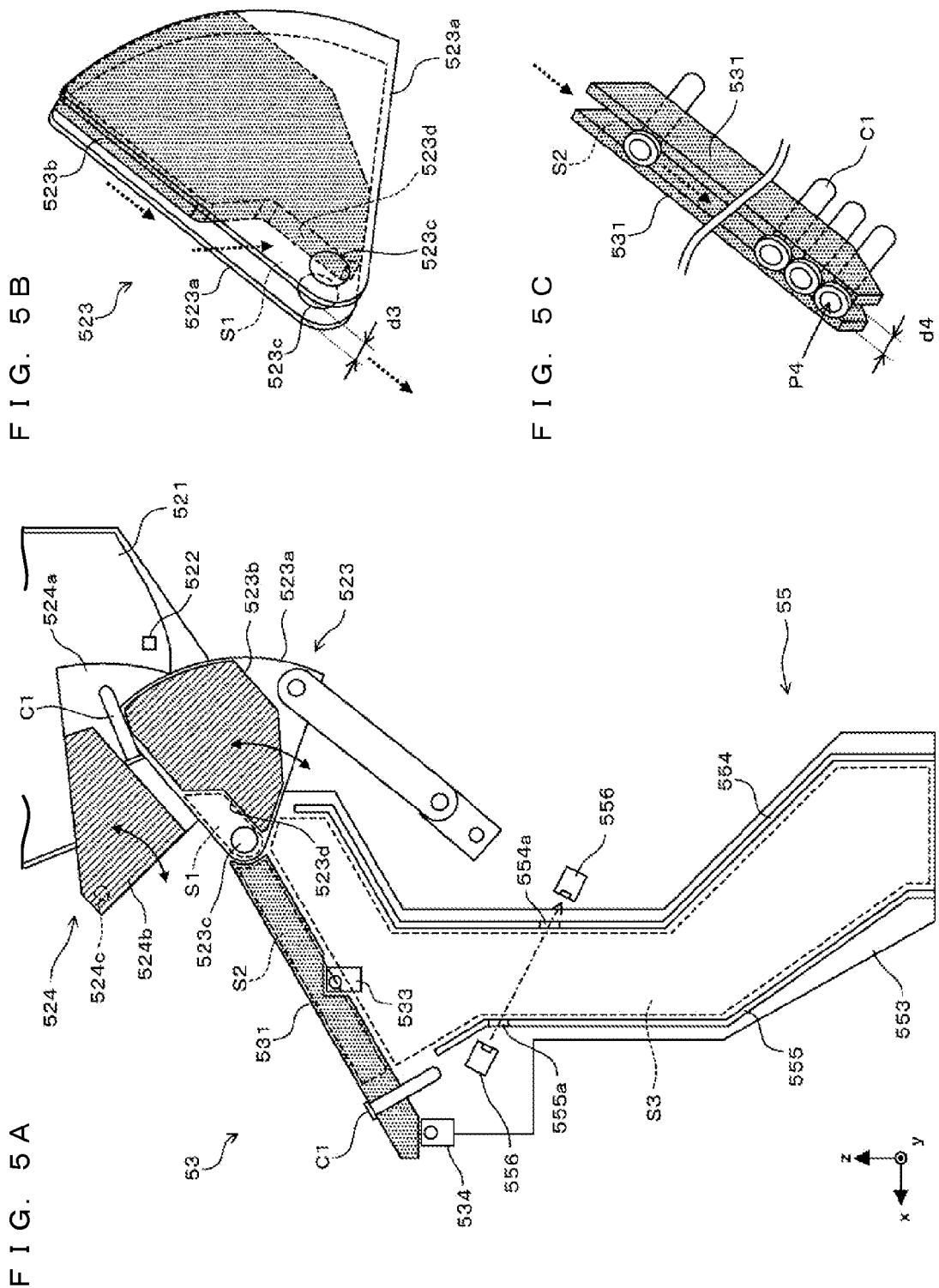

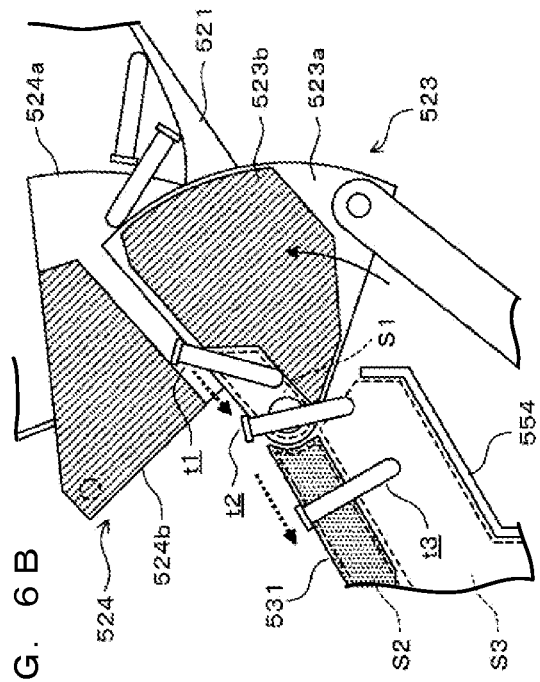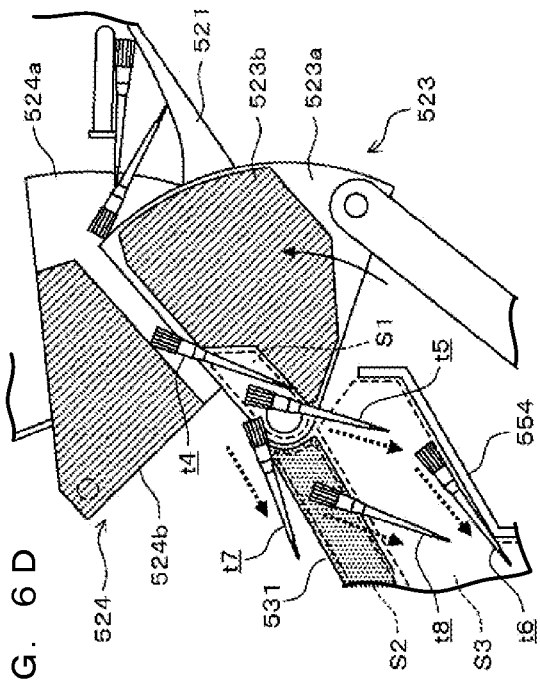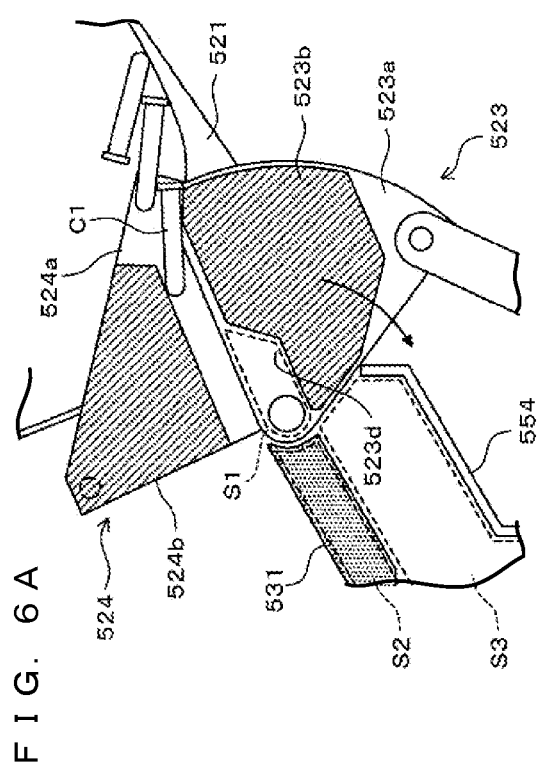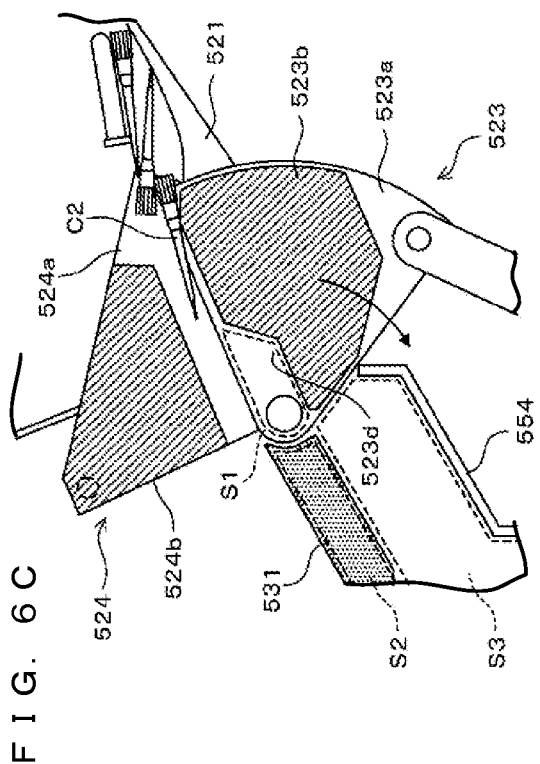

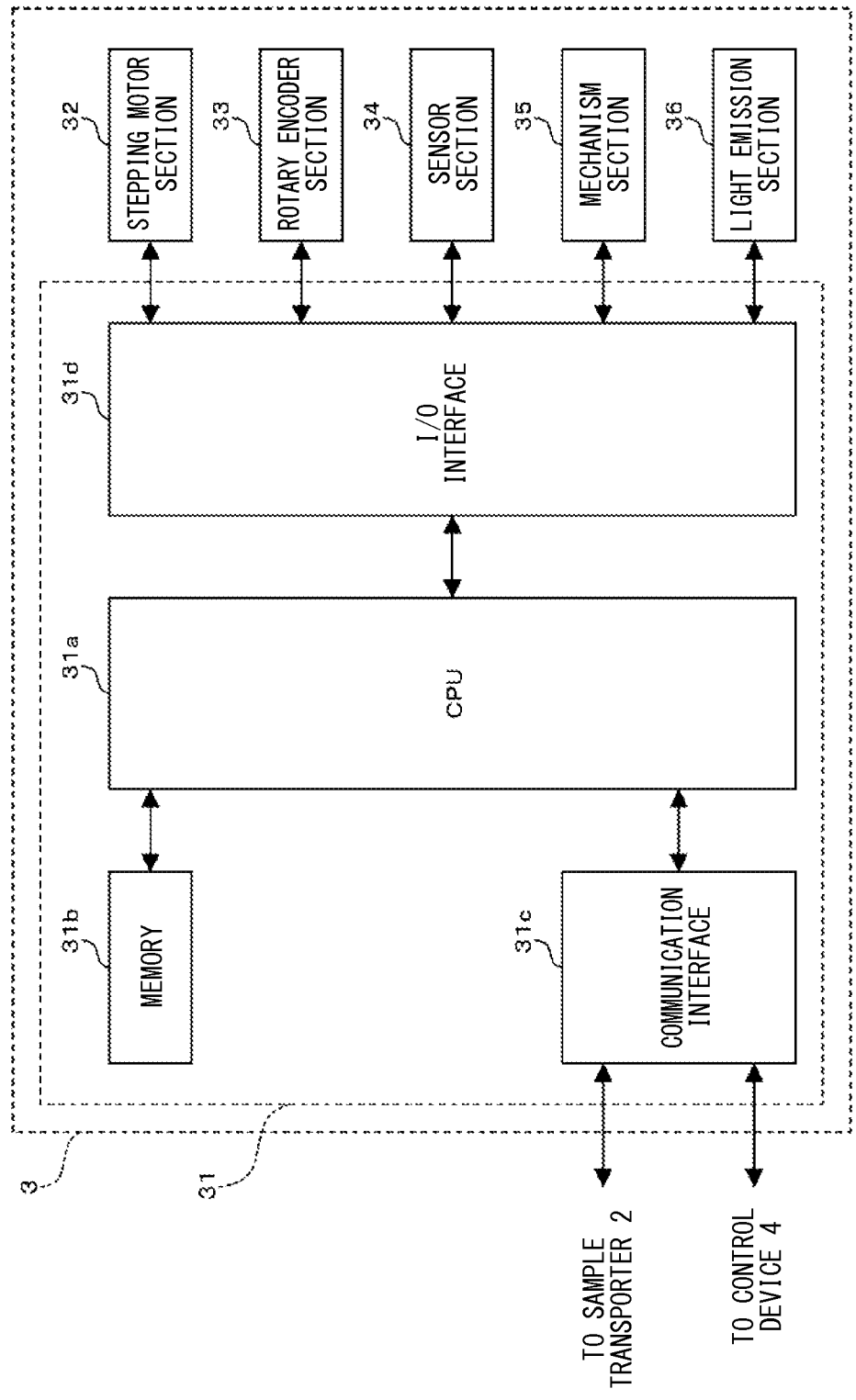
F I G. 7

US 9,285,383 B2

SPECIMEN ANALYZER

FIELD OF THE INVENTION

The present invention relates to specimen analyzers which perform analysis using consumables.

BACKGROUND

To date, there are known analyzers which arrange in a line a large number of randomly housed consumables such as pipette tips and cuvettes, supply the consumables one by one to a predetermined position, and perform analysis using these consumables.

Japanese Laid-Open Patent Application No. 2003-083999 and U.S. Patent Application Publication No. 2011/0086432 disclose automatic analyzers which include a pipette tip supplying unit and a cuvette supplying unit. U.S. Patent Application Publication No. 2011/0086432 describes a cuvette sorting mechanism section which sorts a predetermined quantity of cuvettes one by one, and transfers each sorted cuvette to a predetermined position. These pipette tips and cuvettes are refilled through respective inlets to the analyzer.

SUMMARY OF THE INVENTION

The scope of the present invention is defined solely by the appended claims, and is not affected to any degree by the statements within this summary.

A first aspect of the present invention is a specimen analyzer comprising: a measurement mechanism section configured to measure a specimen by using a first consumable and a second consumable having a shape different from a shape of the first consumable; a first inlet for loading the first consumable; a supplying section configured to supply the first consumable loaded through the first inlet, to the measurement mechanism section; a sorter configured to sort the first consumable and the second consumable from each other; and a storage for housing the second consumable sorted by the sorter.

A second aspect of the present invention is a specimen analyzer comprising: a measurement mechanism section configured to measure a specimen by using a first consumable and a second consumable having a shape different from a shape of the first consumable; a first inlet for loading the first consumable; a supplying section configured to supply the first consumable loaded through the first inlet, to the measurement mechanism section; a sorter configured to sort the first consumable and the second consumable from each other; and a guide part configured to guide the second consumable sorted by the sorter outside.

A third aspect of the present invention is a specimen analyzer comprising: a measurement mechanism section configured to measure a specimen by using a first consumable and a second consumable having a shape different from a shape of the first consumable; a first inlet for loading the first consumable; a supplying section configured to supply the first consumable loaded through the first inlet, to the measurement mechanism section; a sorter configured to sort the first consumable and the second consumable from each other; a sensor which detects the second consumable sorted by the sorter; and a notification part which makes notification of a detection result by the sensor.

BRIEF DESCRIPTION OF THE DRAWINGS

FIGS. 5A-5C show a cross-sectional view of a cuvette supplying section viewed from a side (FIG. 5A) and perspective views (FIG. 5B and FIG. 5C) showing structures of a swing rail and a transfer rail according to an embodiment;

FIG. 6A-6D show a procedure of a cuvette and a tip being sent out by a swing part according to an embodiment;

FIG. 7 shows a configuration of a measurement unit according to an embodiment;

DETAILED DESCRIPTION OF THE PREFERRED EMBODIMENTS

The preferred embodiments of the present invention will be described hereinafter with reference to the drawings.

The present embodiment is realized by applying the present invention to an immune analyzer for performing tests for various items such as hepatitis B, hepatitis C, tumor markers, and thyroid hormones, using samples such as blood.

Figure 1:
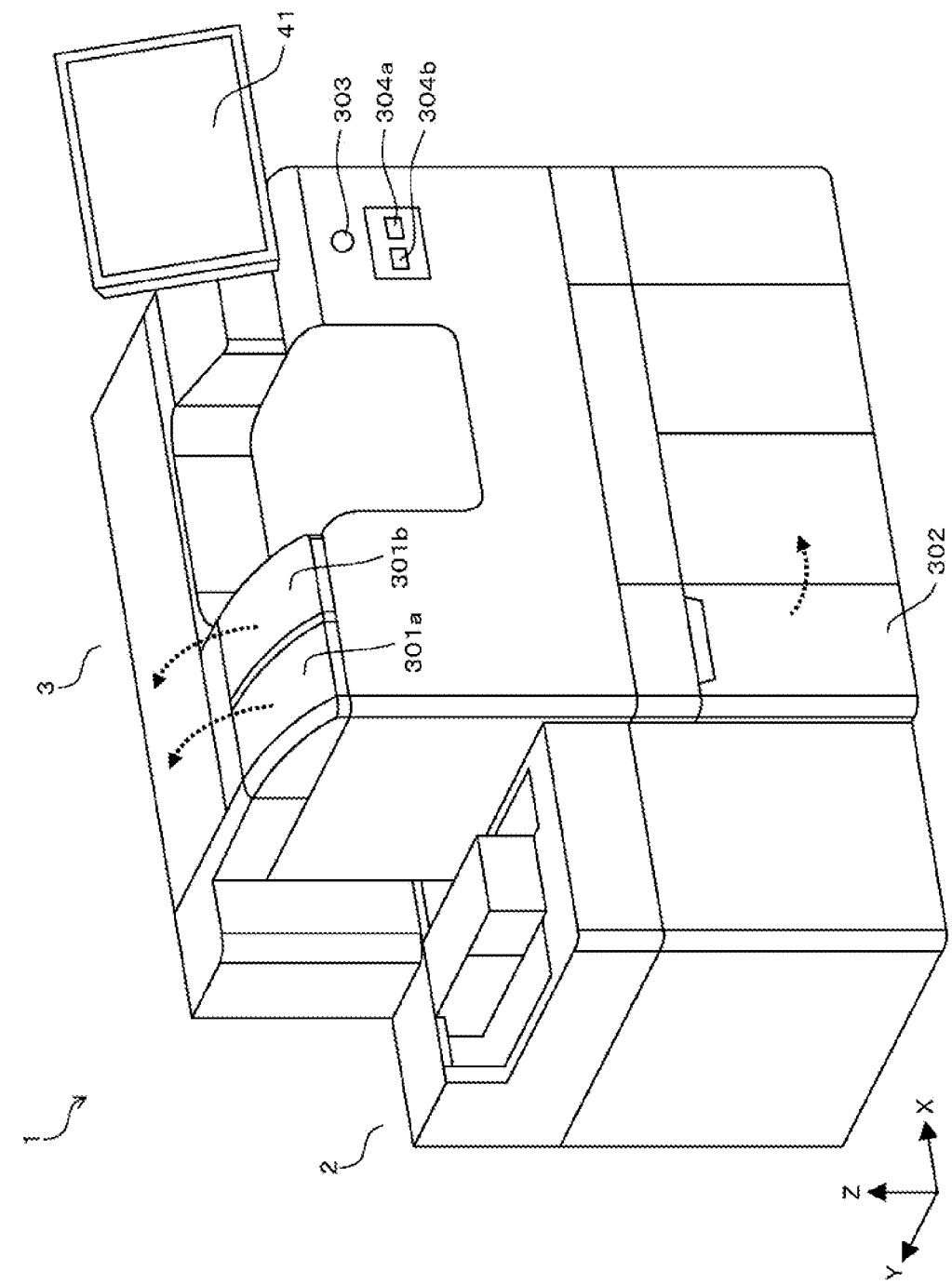
FIG. 1 is a perspective view showing an overall structure of an immune analyzer according to an embodiment.

FIG. 1 is a perspective view showing an overall structure of an immune analyzer 1. The immune analyzer 1 includes a sample transporter 2, a measurement unit 3, and a display input unit 41 implemented by a touch panel.

The sample transporter 2 is configured to be able to transport sample racks each holding sample containers each containing a sample. The measurement unit 3 aspirates a sample from a sample container transported and located at a predetermined position by the sample transporter 2, to perform measurement. In an upper portion and a lower portion of the measurement unit 3, lids 301*a* and 301*b* upwardly openable and a door 302 horizontally openable are formed, respectively.

Figure 2C:
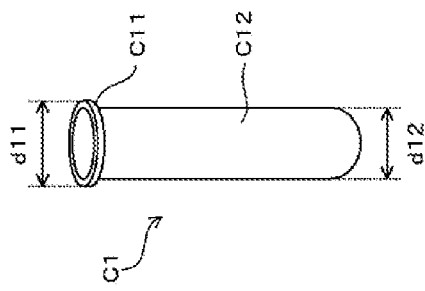
FIGS. 2A-2D show structures of lids (FIG. 2A) and a door (FIG. 2B), and structures of a cuvette (FIG. 2C) and a tip (FIG. 2D) according to embodiment of the invention.
Figure 2D:
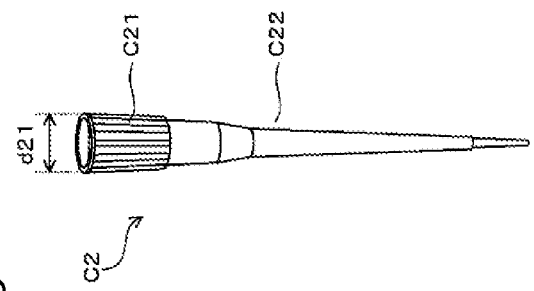
Figure 2A:
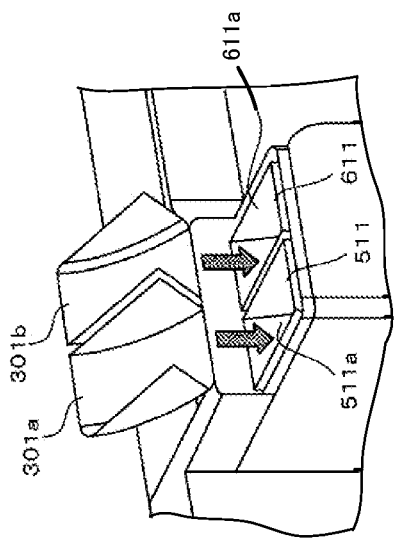

As shown in FIG. 2A, when the lids 301*a* and 301*b* are opened, upper portions of a first hopper 511 and a hopper 611 installed inside the measurement unit 3 become open, respectively. Accordingly, an inlet 511*a* at the upper end of the first hopper 511 and an inlet 611*a* at the upper end of the hopper 611 are exposed to the outside, respectively. A user opens the lid 301*a* and loads cuvettes C1 to be used in measurement operations through the inlet 511*a* into the first hopper 511, and opens the lid 301*b* and loads pipette tips C2 to be used in measurement operations through the inlet 611*a* into the hopper 611.

Figure 2B:
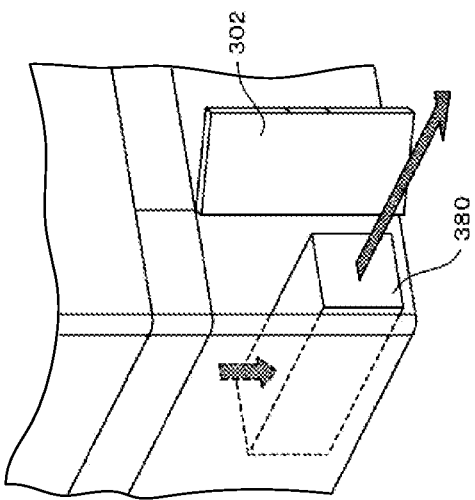

As shown in FIG. 2B, when the door 302 is opened, a portion to the front of a storage 380 set inside the measurement unit 3 becomes open. The storage 380 houses cuvettes C1 and pipette tips C2 that have been used, and is configured to be able to be taken outside via the door 302. The user opens the door 302 to take the storage 380 outside, and discards cuvettes C1 and pipette tips C2 that have been used.

FIGS. 2C and 2D show structures of a cuvette C1 and a pipette tip C2, respectively.

Each cuvette C1 is formed by a flange C11 having a diameter d11, and a body C12 having a diameter d12 which is smaller than the diameter d11. Each pipette tip C2 is formed by an attachment C21 having a diameter d21 which is smaller than the diameter d11, and a body C22 having a diameter which is smaller than the diameter d21.

The cuvette C1 is used in which to react a sample and reagents, and is discarded after measurement of the sample is completed. The pipette tip C2 is used for aspirating and discharging a sample, and is discarded each time aspiration and discharge of a sample are performed. That is, the cuvette C1 and the pipette tip C2 are consumables, and are disposed after use in the measurement unit 3, in order to prevent contamination between samples. Therefore, the user loads cuvettes C1 and pipette tips C2 by the necessary number into the first hopper 511 and the hopper 611, respectively, before starting measurement.

It should be noted that cuvettes C1 and pipette tips C2 are respectively packaged in bags by 500 pieces. The user opens a bag containing cuvettes C1 to load a plurality of cuvettes C1 into the first hopper 511, and opens a bag containing pipette tips C2 to load a plurality of pipette tips C2 into the hopper 611.

With reference back to FIG. 1, an indicator 303, a measurement start button 304a, and an emergency stop button 304b are provided in the front face of the measurement unit 3. The user can start measurement operations by pressing the measurement start button 304a, and can stop all measurement operations in the measurement unit 3 by pressing the emergency stop button 304b. The display input unit 41 displays analysis results of samples and receives instructions from the user.

Figure 3:
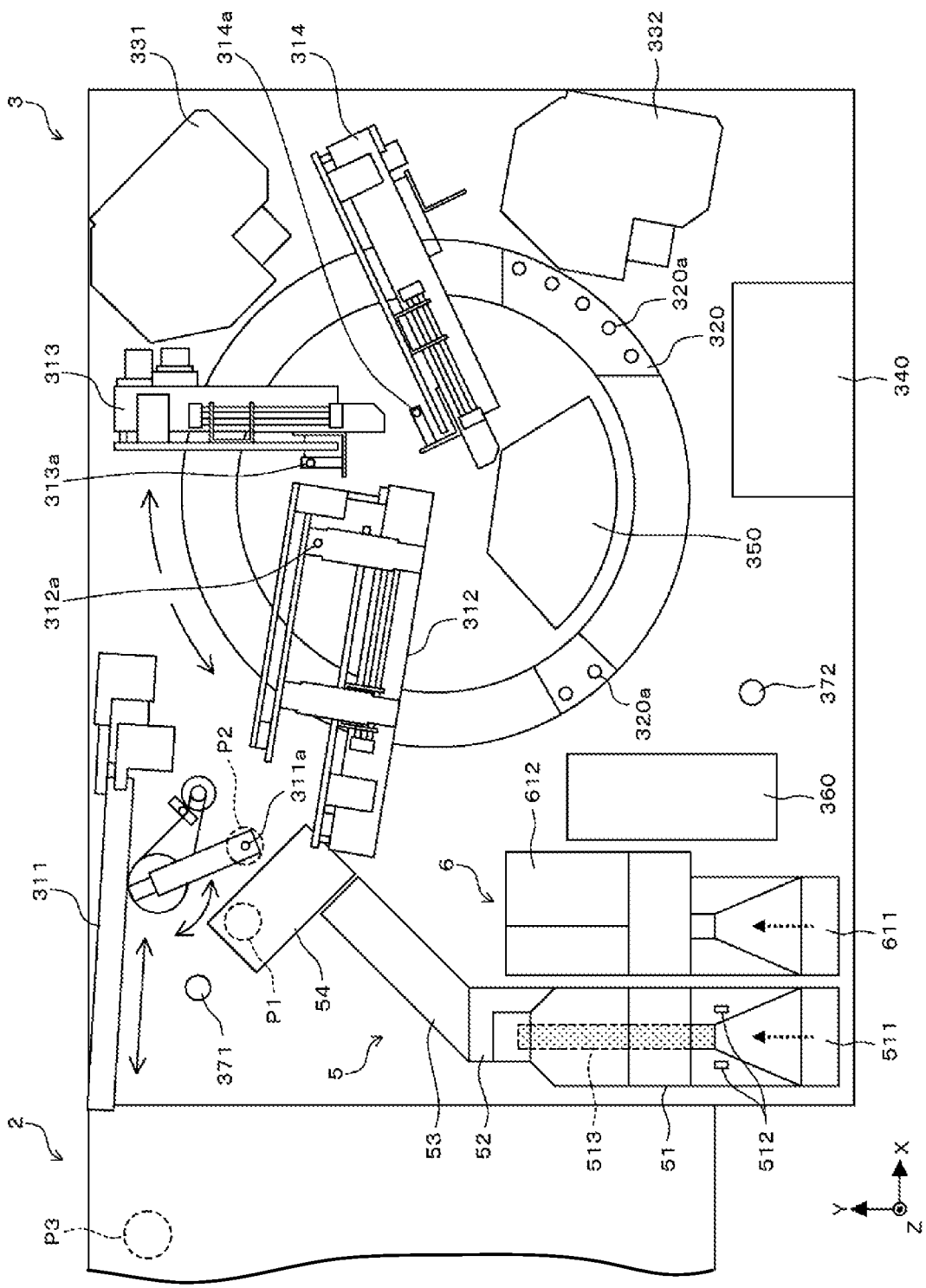
FIG. 3 is a plan view showing a structure of a measurement unit according to an embodiment, viewed from above.

FIG. 3 is a plan view showing a structure of the measurement unit 3 viewed from above.

The measurement unit 3 includes a cuvette supplying section 5 and a tip supplying section 6. The measurement unit 3 also includes a sample dispensing arm 311, an R1 reagent dispensing arm 312, an R2 reagent dispensing arm 313, an R3 reagent dispensing arm 314, a reaction part 320, a primary BF (Bound Free) separator 331, a secondary BF separator 332, an R4/R5 reagent feeder 340, a reagent setting part 350, and a detector 360, as a measurement mechanism section for performing sample measurement by using cuvettes C1 supplied from the cuvette supplying section 5 and pipette tips C2 supplied from the tip supplying section 6. The measurement unit 3 is also provided with disposal holes 371 and 372.

In the immune analyzer 1, a sample such as blood to be measured and a buffer solution (R1 reagent) are mixed together, and to the obtained mixture solution, a reagent (R2 reagent) is added that contains magnetic particles supporting a capture antibody to be bound to an antigen contained in the sample. By attracting magnetic particles supporting the capture antibody bound to the antigen to a magnet in the primary BF separator 331, components in the sample that were not bound to the capture antibody are removed. Then, a labeled antibody (R3 reagent) is further added thereto. Thereafter, by attracting magnetic particles supporting the capture antibody bound to the antigen and the labeled antibody to a magnet in the secondary BF separator 332, the R3 reagent containing the labeled antibody that did not react is removed. Further, a dispersion liquid (R4 reagent) and a luminescent substrate (R5 reagent) that emits light in the course of the reaction with the labeled antibody are added thereto. Then, an amount of light generated in the reaction between the labeled antibody and the luminescent substrate is measured. Through these process steps, the antigen contained in the sample and bound to the labeled antibody is quantitatively measured.

The cuvette supplying section 5 includes a first reservoir 51, a second reservoir 52, a transfer part 53, and a take-out part 54. It should be noted that a guide part 55 (see FIG. 4) is provided below (Z axis negative direction side) the transfer part 53 of the cuvette supplying section 5.

The first reservoir 51 includes the first hopper 511, a sensor 512 composed of a light emitter and a light receiver, and a circulating belt 513. The first hopper 511 is provided with a slope in the bottom surface thereof, and cuvettes C1 loaded into the first hopper 511 are held in the first hopper 511, sequentially stacked from the bottom surface thereof. The sensor 512 detects cuvettes C1 located on the bottom surface of the first hopper 511. The belt 513 transfers cuvettes C1 held in the first hopper 511 to the second reservoir 52.

The cuvettes C1 transferred to the second reservoir 52 are transferred through the second reservoir 52, the transfer part 53, and the take-out part 54, to be supplied one by one to a reagent discharging position P1 for the R1 reagent dispensing arm 312. Detailed structure of the cuvette supplying section 5 will be described later with reference to FIG. 4 and FIGS. 5A to 5C.

The tip supplying section 6 includes the hopper 611 and a transfer part 612, and supplies one by one pipette tips C2 loaded from the hopper 611, to a tip attaching position (not shown) for the sample dispensing arm 311, by means of the transfer part 612. The pipette tip C2 located at the tip attaching position is attached to the tip of a pipette 311a of the sample dispensing arm 311.

The R1 reagent dispensing arm 312 aspirates an R1 reagent set in the reagent setting part 350 and discharges the aspirated R1 reagent into the cuvette C1 at the reagent discharging position P1, by using a pipette 312a. The cuvette C1 into which the R1 reagent has been discharged is located at a position P2 for a sample by a catcher not shown. The sample dispensing arm 311 aspirates a sample in a sample container transported to a position P3 by the sample transporter 2, and discharges the aspirated sample into the cuvette C1 at the position P2, by using the attached pipette tip C2. This cuvette C1 is transferred to the reaction part 320 by a catcher not shown. When dispensing of one sample by the sample dispensing arm 311 is completed, the pipette tip C2 used in the dispensing of this sample is discarded into the disposal hole 371.

The R2 reagent dispensing arm 313 aspirates an R2 reagent set in the reagent setting part 350 and discharges the aspirated R2 reagent into the cuvette C1 containing the R1 reagent and the sample, by using a pipette 313a.

The reaction part 320 is formed in an annular shape so as to surround the reagent setting part 350, and has a plurality of cuvette setting parts 320a arranged at predetermined intervals along the outer shape of the reagent setting part 350. Further, the reaction part 320 is configured to be rotatable, and moves cuvette setting parts 320a to their process positions at which various processes (such as dispensing of a reagent) are performed. Each cuvette C1 set in the cuvette setting part 320a is heated to about 42° C. Accordingly, reaction between the sample and various reagents in the cuvette C1 is promoted.

The cuvette C1 containing the sample, the R1 reagent, and the R2 reagent is transferred by a catcher not shown, from the reaction part 320 to the primary BF separator 331. The primary BF separator 331 removes components in the sample that were not bound to the capture antibody, from the specimen in the cuvette C1. The R3 reagent dispensing arm 314 aspirates an R3 reagent set in the reagent setting part 350 and discharges the aspirated R3 reagent into the cuvette C1 transferred to the reaction part 320 from the primary BF separator 331, by using a pipette 314a.

The cuvette C1 containing the R3 reagent and the specimen after being subjected to the removal process by the primary BF separator 331 is transferred from the reaction part 320 to the secondary BF separator 332, by a catcher not shown. The secondary BF separator 332 removes the R3 reagent containing the labeled antibody that did not react. The R4/R5 reagent feeder 340 dispenses an R4 reagent and an R5 reagent sequentially into the cuvette C1 containing the specimen after the removal process by the secondary BF separator 332, by means of a tube not shown.

The detector 360 obtains, by means of a photo multiplier tube, light generated in the reaction process between the luminescent substrate and the labeled antibody bound to the antigen in the sample that has been subjected to the predetermined processes in the cuvette C1, thereby measuring the amount of the antigen contained in the sample. When the measurement of one sample by the detector 360 is completed, the cuvette C1 containing this sample is discarded into the disposal hole 372 by a catcher not shown.

The disposal holes 371 and 372 are connected to a disposal channel continuing to the storage 380 shown in FIG. 2B. Pipette tips C2 discarded into the disposal hole 371 and cuvettes C1 discarded into the disposal hole 372 are housed in the storage 380 through the disposal channel.

Here, as shown in FIG. 2A, when the user opens the lid 301a and loads cuvettes C1 into the first hopper 511, a case could occur where the user loads pipette tips C2 by mistake. In this case, there is a risk in which such pipette tips C2 loaded by mistake are transferred by the cuvette supplying section 5 and the pipette tips C2 get stuck inside the cuvette supplying section 5. Moreover, there is a risk in which the pipette tips C2 loaded by mistake are transferred even to the inside of the measurement unit 3 by the cuvette supplying section 5. In such a case, complicated restoration operations are necessary in order to remove the pipette tips C2.

Therefore, in the immune analyzer 1 of the present embodiment, the cuvette supplying section 5 is configured such that cuvettes C1 and pipette tips C2 can be sorted from each other even when pipette tips C2 are loaded by mistake into the first hopper 511. Hereinafter, description will be given of sorting of cuvettes C1 and pipette tips C2 from each other as well as the structure of the cuvette supplying section 5.

Figure 4:
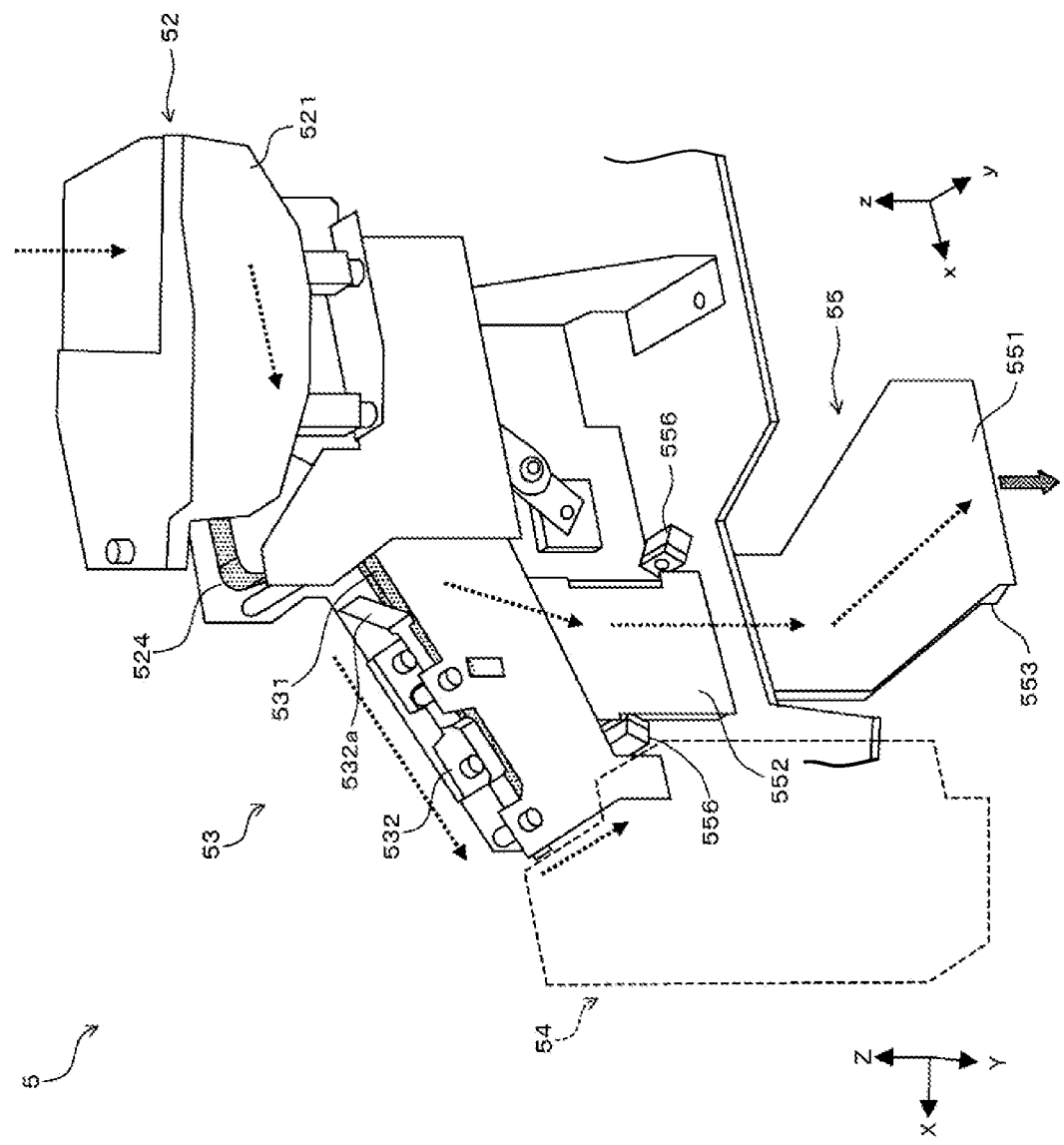
FIG. 4 is a perspective view showing a structure of a cuvette supplying section according to an embodiment.

FIG. 4 is a perspective view showing the structure of the cuvette supplying section 5. FIG. 5A is a cross-sectional view when the cuvette supplying section 5 is viewed from a side thereof. FIGS. 5B and 5C are perspective views showing structures of a swing rail 523 and transfer rails 531, respectively. It should be noted that, in FIG. 4, the first reservoir 51 is not shown for convenience. In FIG. 4 and FIG. 5A, coordinate axes (xyz) different from the coordinate axes (XYZ) shown in FIG. 1 and FIG. 3 are shown.

First, description will be given of the procedure of cuvettes C1 being transferred by the cuvette supplying section 5 as well as the structure of the cuvette supplying section 5.

The cuvettes C1 loaded into the first hopper 511 of the first reservoir 51 are transferred to the second reservoir 52 by the belt 513 (see FIG. 3) as described above.

With reference to FIG. 4 and FIG. 5A, the second reservoir 52 includes a second hopper 521, a sensor 522 composed of a light emitter and a light receiver, the swing rail 523, and a swing guide 524. The second hopper 521 is provided with a slope in the bottom surface thereof. To the second hopper 521, cuvettes C1 are transferred from the first reservoir 51 such that several cuvettes C1 are held in the second hopper 521. The cuvettes C1 transferred from the first reservoir 51 are held in the second hopper 521, sequentially stacked from the bottom surface thereof. The sensor 522 detects cuvettes C1 located on the bottom surface of the second hopper 521.

With reference to FIGS. 5A and 5B, the swing rail 523 includes a pair of fan-shaped plates 523a, and a spacer 523b fixed to the pair of plates 523a so as to be sandwiched therebetween. An interval d3 (thickness of the spacer 523b) between the pair of plates 523a is smaller than the diameter d11 of the flange C11 of each cuvette C1, and greater than the diameter d12 of the body C12. Further, a shaft hole 523c is formed in each of the pair of plates 523a. The shaft hole 523c in the plate 523a on the y axis negative direction side is supported by a shaft from the y axis negative direction side, and the shaft hole 523c in the plate 523a on the y axis positive direction side is supported by a shaft from the y axis positive direction side. Accordingly, the swing rail 523 can rotate about the y axis. Further, a cutout 523d is formed in the spacer 523b, and a space S1 is formed by the pair of plates 523a and the spacer 523b. It should be noted that the space S1 corresponds to the "gap" described in claims.

The swing guide 524 includes a pair of fan-shaped plates 524a in contact with the outer sides of the swing rail 523, and a spacer 524b fixed to the pair of plates 524a so as to be sandwiched therebetween. A shaft hole 524c is formed in each of the pair of plates 524a, and the pair of plates 524a are respectively supported by shafts from the y axis negative direction side and the y axis positive direction side. Accordingly, the swing guide 524 can rotate about the y axis.

The swing rail 523 and the swing guide 524 structured as above are coupled to each other so as to be rotatable in an integrated manner. Each cuvette C1 is sent out to the transfer rails 531 of the transfer part 53 through the space between the swing rail 523 and the spacer 524b of the swing guide 524, by the swing rail 523 and the swing guide 524 being swung.

With reference to FIG. 4 and FIGS. 5A and 5C, the transfer part 53 includes the pair of transfer rails 531, a cover 532, and sensors 533 and 534 of a reflection-type. An interval d4 between the pair of transfer rails 531 is the same as the interval d3 between the pair of plates 523a. A space S2 is formed by the interval d4 provided between the pair of transfer rails 531. It should be noted that the space S2 corresponds to the "gap" described in claims.

The cuvettes C1 sent out by the swing rail 523 and the swing guide 524 (hereinafter, collectively referred to as a "swing part") slip down by their own weights along the upper sides of the pair of transfer rails 531, and are sequentially arranged in a line from the lower end of the transfer rails 531. At this time, the body C12 of each cuvette C1 enters the space S2, and only the flange C11 is supported by the upper sides of the pair of transfer rails 531.

The cover 532 is provided in order to protect a portion above the transfer rails 531. In the right end of the cover 532, a stopper 532a bent upward is formed. The sensors 533 and 534 are installed near the middle portion of the transfer rails 531 and near the lowest portion of the transfer rails 531, respectively. The sensor 533 detects a cuvette C1 at the front (y axis positive direction) position (middle position of the transfer rails 531) of the sensor 533, and the sensor 534 detects a cuvette C1 at the front (y axis positive direction) position (lowest position P4 of the transfer rails 531) of the sensor 534.

FIGS. 6A and 6B show the procedure of cuvettes C1 on the bottom surface of the second hopper 521 being sent out by the swing part.

First, the swing rail 523 and the swing guide 524 are rotated downward to be located at a position shown in FIG. 6A. Accordingly, one cuvette C1 located on the bottom surface of the second hopper 521 is drawn into the space between the swing rail 523 and the spacer 524b.

Subsequently, the swing rail 523 and the swing guide 524 are rotated upward to be located at a position shown in FIG. 6B. Accordingly, the cuvette C1 drawn into the space between the swing rail 523 and the spacer 524b slips down by its own weight along the upper sides (end portions facing the spacer 524b) of the pair of plates 523a, to be sent out onto the pair of transfer rails 531.

At this time, when the cuvette C1 slipping down comes to the space 51, as shown by the cuvette C1 at a position t1, the flange C11 is supported by the upper sides of the pair of plates 523a, and the body C12 enters the space 51. When the cuvette C1 at the position t1 further slips down by its own weight, as in the case of the position t1, the flange C11 is supported by the upper sides of the pair of plates 523a to be located at a position t2, with the body C12 being in the space 51. When the cuvette C1 at the position t2 further slips down by its own weight, as in the cases of the positions t1 and t2, the flange C11 is supported by the pair of transfer rails 531 to be located at a position t3, with the body C12 being in the space S2.

It should be noted that FIGS. 6A and 6B have described a case where the cuvette C1 enters the space between the swing rail 523 and the spacer 524b with the body C12 side first. However, even in a case where the cuvette C1 enters the space between the swing rail 523 and the spacer 524b with the flange C11 side first as shown in FIG. 5A, the cuvette C1 is sent out to the transfer rails 531 as in the case described above. That is, with respect to the cuvette C1 that has come to the space S1 with the flange C11 side first, the flange C11 is supported by the upper sides of the pair of plates 523a and the body C12 enters the space S1 as in the case described above. Thus, with respect to the cuvette C1 sent out to the transfer rails 531, the flange C11 is supported by the transfer rails 531 as described above.

With reference to FIG. 4, the take-out part 54 stops a cuvette C1 located at the lowest position on the transfer rails 531. When a cuvette C1 is needed in a measurement operation, the take-out part 54 transports, among cuvettes C1 arranged along the transfer rails 531, only the cuvette C1 located at the lowest position to the reagent discharging position P1 (see FIG. 3).

Next, description will be given of the procedure of transferring pipette tips C2 that were loaded by mistake into the first hopper 511, as well as the structure of the guide part 55.

Pipette tips C2 loaded by mistake into the first hopper 511 of the first reservoir 51 are transferred to the second reservoir 52 by the belt 513 (see FIG. 3), as in the case of the cuvettes C1. The pipette tips C2 transferred from the first reservoir 51 are held in the second hopper 521, sequentially stacked from the bottom surface thereof, as in the case of the cuvettes C1.

With reference to FIG. 4 and FIG. 5A, the guide part 55 is provided below the transfer part 53, and includes plates 551, 552, and 553, walls 554 and 555, and a sensor 556 composed of a light emitter and a light receiver. FIG. 5A shows a state where the plates 551 and 552 have been removed. The walls 554 and 555 have a plurality of flat parts perpendicular to an xz plane. The plates 551 to 553 and the walls 554 and 555 form a space S3. The space S3 is connected to the disposal channel continuing to the storage 380.

Further, the walls 554 and 555 have holes 554a and 555a formed therein, respectively. The sensor 556 can detect a pipette tip C2 passing through the space S3, via the holes 554a and 555a.

FIGS. 6C and 6D show the procedure of pipette tips C2 on the bottom surface of the second hopper 521 being sent out by the swing part.

When the swing rail 523 and the swing guide 524 are rotated downward, as shown in FIG. 6C, a pipette tip C2 located on the bottom surface of the second hopper 521 is drawn into the space between the swing rail 523 and the spacer 524b. Subsequently, when the swing rail 523 and the swing guide 524 are rotated upward, as shown in FIG. 6D, the pipette tip C2 drawn into the space between the swing rail 523 and the spacer 524b slips down by its own weight along the upper sides of the pair of plates 523a.

At this time, when the pipette tip C2 slipping down comes to the space 51, as shown by the pipette tip C2 at a position t4, the pipette tip C2 enters the space 51. As described above, the interval d3 between the pair of plates 523a is greater than the diameters of the attachment C21 and the body C22 of the pipette tip C2. Therefore, the pipette tip C2 at the position t4 passes through the space 51 to be located at a position t5. When the pipette tip C2 at the position t5 further slips down by its own weight, the pipette tip C2 enters the space S3, and slips down along the wall 554.

In a case where a pipette tip C2 swiftly slips down along the upper sides of the pair of plates 523a, for example, the pipette tip C2 may come to the transfer rails 531, as shown by a pipette tip C2 at a position t7. Also in this case, as described above, since the interval d4 between the pair of transfer rails 531 is greater than the diameters of the attachment C21 and the body C22 of the pipette tip C2, the pipette tip C2 at the position t7 passes through the space S2 to be located at a position t8. The pipette tip C2 at the position t8 further falls down to enter the space S3, and slips down along the wall 554, as in the case of the pipette tip C2 at a position t6.

It should be noted that cuvettes C1 on the transfer rails 531 are arranged up to the front (y axis positive direction) position of the sensor 533, and are not arranged up to a position higher than the front position of the sensor 533. Moreover, the cover 532 in which the stopper 532a is formed is provided over the transfer rails 531, as shown in FIG. 4. Therefore, a pipette tip C2 having swiftly slipped down from the upper side of the pair of plates 523a passes through the space S2 without bumping a cuvette C1, to be sent to the space S3.

With reference back to FIG. 4 and FIG. 5A, the pipette tip C2 that has been sent to the space S3 and has slipped down along the wall 554 further falls downward within the space S3, is detected by the sensor 556, and then is discharged from a lower portion of the guide part 55. The pipette tip C2 discharged from the lower portion of the guide part 55 is sent to the disposal channel which continues from the disposal holes 371 and 372 to the storage 380. In this manner, the pipette tips C2 loaded by mistake into the first hopper 511 are housed in the storage 380.

FIG. 7 shows a configuration of the measurement unit 3.

The measurement unit 3 includes a control section 31, a stepping motor section 32, a rotary encoder section 33, a sensor section 34, a mechanism section 35, and a light emission section 36. The control section 31 includes a CPU 31a, a memory 31b, a communication interface 31c, and an I/O interface 31d.

The CPU 31a executes computer programs stored in the memory 31b. Moreover, the CPU 31a receives, via the I/O interface 31d, signals from the stepping motor section 32, the rotary encoder section 33, the sensor section 34, the mechanism section 35, and the light emission section 36, and controls these components. The memory 31b has stored therein various computer programs necessary for measurement operations, and is also used as a work area for the CPU 31a.

The communication interface 31c is connected to the sample transporter 2 and a control device 4. The CPU 31a transmits instruction signals to the sample transporter 2 via the communication interface 31c, and receives instruction signals transmitted from the sample transporter 2. Further, the CPU 31a transmits instruction signals and optical information (such as data of the amount of light generated in the reaction between the labeled antibody and the luminescent substrate) of samples to the control device 4 via the communication interface 31c, and receives instruction signals transmitted from the control device 4 via the communication interface 31c.

The stepping motor section 32 includes stepping motors for driving the belt 513, the swing rail 523 and the swing guide 524 which are integrated with each other, and the take-out part 54, and other stepping motors in the measurement unit 3. The rotary encoder section 33 includes rotary encoders corresponding to the stepping motors included in the stepping motor section 32.

The sensor section 34 includes a sensor for detecting that the measurement start button 304a or the emergency stop button 304b has been pressed, the sensor 512 of the first reservoir 51, the sensor 522 of the second reservoir 52, the sensors 533 and 534 of the transfer part 53, the sensor 556 of the guide part 55, and other sensors in the measurement unit 3. The mechanism section 35 includes mechanisms for driving components in the measurement unit 3. The light emission section 36 includes an LED for causing the indicator 303 (see FIG. 1) to emit light.

Figure 8:
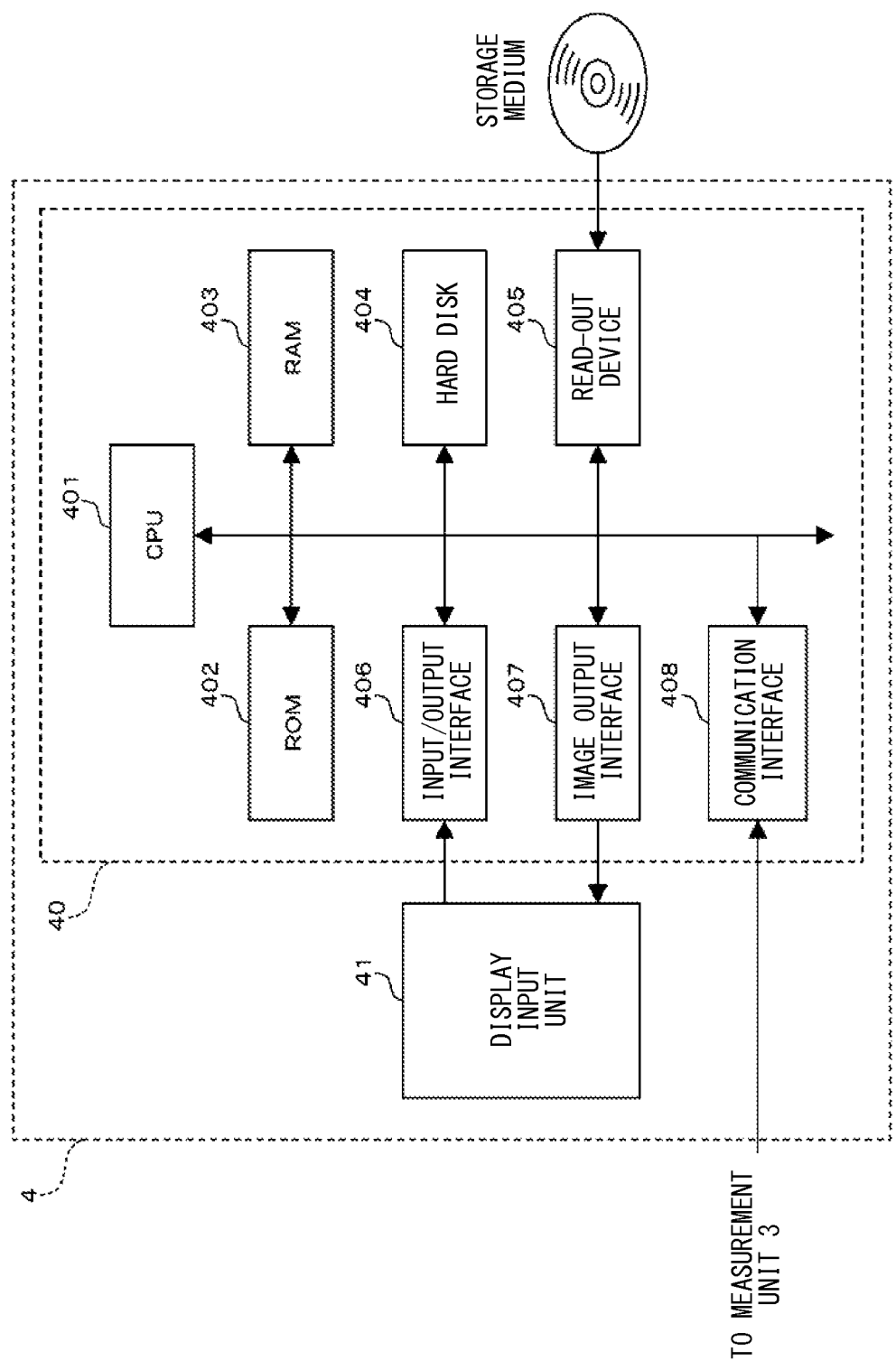
FIG. 8 shows a configuration of a control device according to an embodiment.

FIG. 8 shows a configuration of the control device 4.

The control device 4 is implemented by a personal computer, and includes a body 40 and the display input unit 41. The body 40 includes a CPU 401, a ROM 402, a RAM 403, a hard disk 404, a read-out device 405, an input/output interface 406, an image output interface 407, and a communication interface 408.

The CPU 401 executes computer programs stored in the ROM 402 and computer programs loaded onto the RAM 403. The RAM 403 is used for reading out computer programs stored in the ROM 402 and the hard disk 404. The RAM 403 is also used as a work area for the CPU 401 when the CPU 401 executes these computer programs.

The hard disk 404 has stored therein computer programs to be executed by the CPU 401 such as an operating system and application programs, and data used for execution of such computer programs. The read-out device 405 is implemented by a CD drive, a DVD drive, or the like, and can read out computer programs and data stored in storage mediums.

The input/output interface 406 receives signals outputted from the display input unit 41. The image output interface 407 outputs video signals corresponding to image data to the display input unit 41. The display input unit 41 displays an image based on the video signals outputted from the image output interface 407, and outputs instructions received from the user via the screen of the display input unit 41, to the input/output interface 406.

The communication interface 408 is connected to the measurement unit 3. The CPU 401 transmits instruction signals to the measurement unit 3 via the communication interface 408, and receives instruction signals transmitted from the measurement unit 3 via the communication interface 408.

Figure 9:
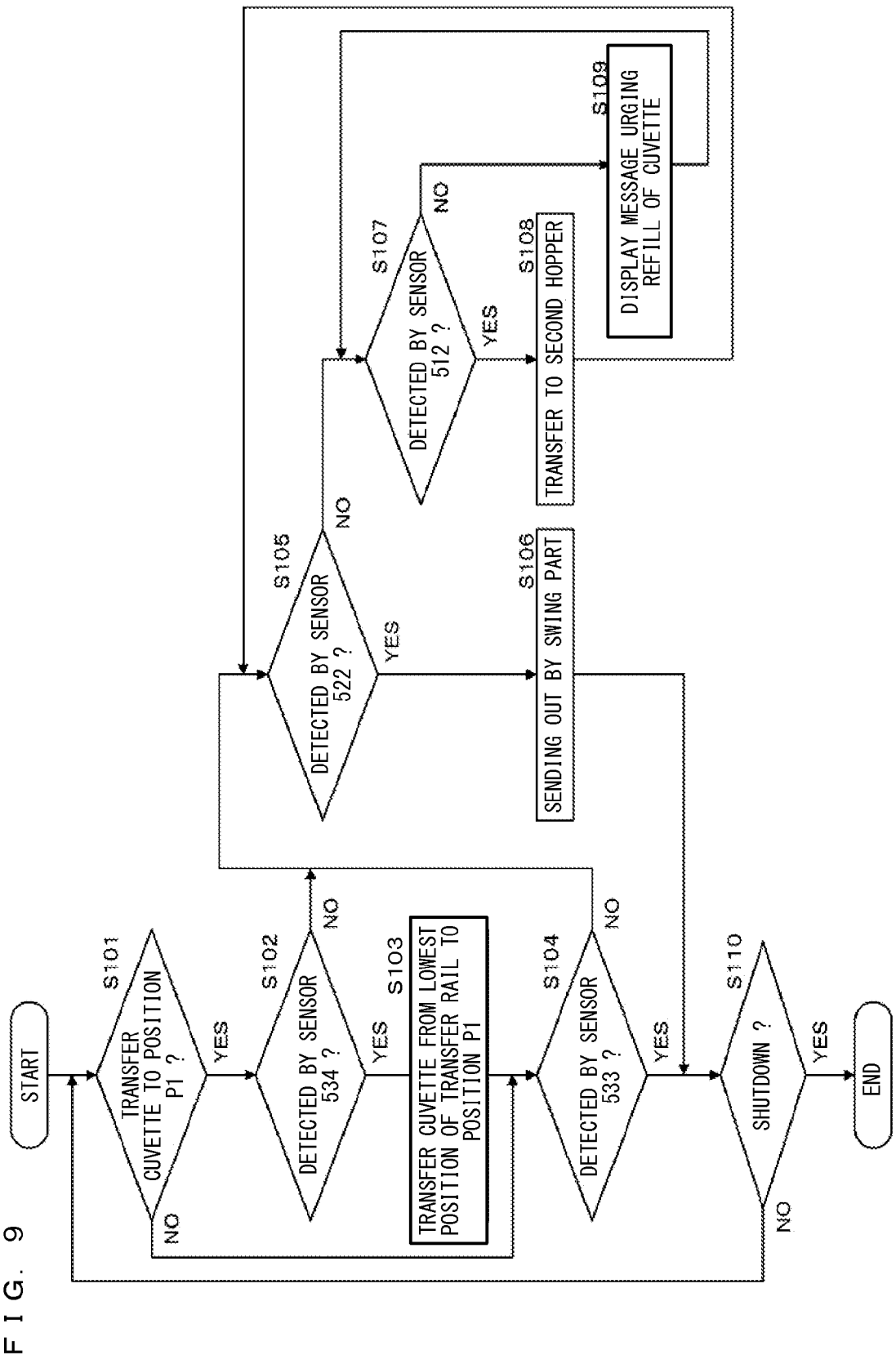
FIG. 9 is a flow chart showing control of a cuvette supplying section regarding transfer of cuvettes according to an embodiment.

FIG. 9 is a flow chart showing control of the cuvette supplying section 5 regarding transfer of cuvettes C1.

The CPU 31a of the measurement unit 3 determines whether it is necessary to transfer a cuvette C1 to the reagent discharging position P1 in order for the R1 reagent to be discharged (S101). When it is not necessary to transfer a cuvette C1 to the reagent discharging position P1 (S101: NO), the processing is advanced to S104. When it is necessary to transfer a cuvette C1 to the reagent discharging position P1 (S101: YES), the CPU 31a determines whether there is a cuvette C1 at the lowest position P4 of the transfer rails 531 based on a detection signal from the sensor 534 (S102).

When there is no cuvette C1 at the lowest position P4 (S102: NO), the processing is advanced to S105. When there is a cuvette C1 at the lowest position P4 (S102: YES), the CPU 31a causes this cuvette C1 to be transferred to the reagent discharging position P1 (S103). Subsequently, the CPU 31a determines whether there is a cuvette C1 at the middle position of the transfer rails 531 based on a detection signal from the sensor 533 (S104). It should be noted that if the sensor 533 has been detecting a cuvette C1 for a predetermined time period, the CPU 31a determines that there is a cuvette C1 at the middle position.

When there is a cuvette C1 at the middle position (S104: YES), the CPU 31a returns the processing to S101, and continues the processes of S101 to S109 until a shutdown instruction is issued (S110). When there is no cuvette C1 at the middle position (S104: NO), the CPU 31a determines whether there are cuvettes C1 or pipette tips C2 on the bottom surface of the second hopper 521 based on a detection signal from the sensor 522 (S105).

When there are cuvettes C1 or pipette tips C2 on the bottom surface of the second hopper 521 (S105: YES), the CPU 31a causes the swing part to perform the sending out as described above, to send out a cuvette C1 or a pipette tip C2 on the bottom surface of the second hopper 521 (S106). As described above, in a case where a cuvette C1 has been sent out, this cuvette C1 is transferred along the transfer rails 531, and in a case where a pipette tip C2 has been sent out, this pipette tip C2 is sent to the space S3. Then, the processing is advanced to S110. On the other hand, when there is neither a cuvette C1 nor a pipette tip C2 on the bottom surface of the second hopper 521 (S105: NO), the CPU 31a determines whether there are cuvettes C1 or pipette tips C2 on the bottom surface of the first hopper 511 based on a detection signal from the sensor 512 (S107).

When there are cuvettes C1 or pipette tips C2 on the bottom surface of the first hopper 511 (S107: YES), the CPU 31a drives the belt 513 to transfer cuvettes C1 or pipette tips C2 on the bottom surface of the first hopper 511 to the second hopper 521 (S108). Then, the processing is returned to S105. On the other hand, when there is neither a cuvette C1 nor a pipette tip C2 on the bottom surface of the first hopper 511 (S107: NO), the CPU 31a causes a message that urges refill of cuvettes C1 to be displayed (S109). That is, the CPU 31a lights the indicator 303 in red and transmits an instruction signal to the control device 4. Upon receiving this instruction signal, the control device 4 causes the display input unit 41 to display a message for urging the user to refill cuvettes C1. Then, the processing is returned to S107. When cuvettes C1 are refilled, the color of the indicator 303 is returned to the color at normal operation.

Figure 10:
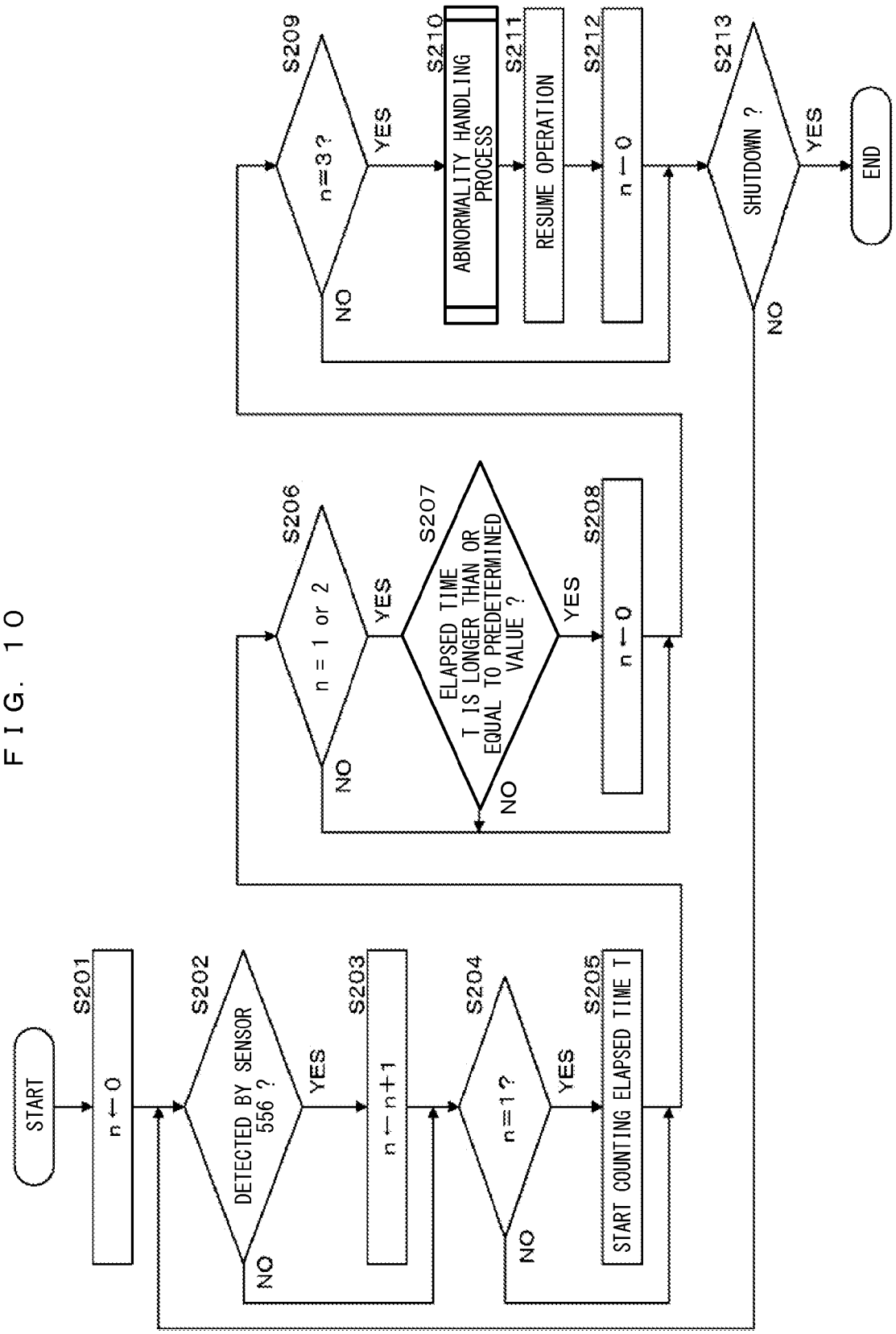
FIG. 10 is a flow chart showing control of a cuvette supplying section regarding tips loaded by mistake according to an embodiment.

FIG. 10 is a flow chart showing control of the cuvette supplying section 5 regarding pipette tips C2 loaded by mistake. It should be noted that the control shown in FIG. 10 is performed in parallel with the control shown in FIG. 9.

Upon activation of the immune analyzer 1, the CPU 31a of the measurement unit 3 assigns 0 to a variable n for counting pipette tips C2 in the memory 31b (S201). Subsequently, the CPU 31a determines whether a pipette tip C2 has been sent to the space S3 based on a detection signal from the sensor 556 (S202). When a pipette tip C2 has been sent to the space S3 (S202: YES), the CPU 31a increments the value of n by 1 (S203).

Next, when the value of n is 1 (S204: YES), the CPU 31a starts counting elapsed time T (S205). That is, the elapsed time T since the timing at which a pipette tip C2 loaded by mistake entered the space S3 for the first time is counted.

Next, when the value of n is 1 or 2 (S206: YES), the CPU 31a determines whether the elapsed time T is longer than or equal to a predetermined value (e.g., 3 minutes) (S207). When the elapsed time T is longer than or equal to the predetermined value (S207: YES), the CPU 31a returns the value of n to 0. For example, in a case where the number of pipette tips C2 loaded by mistake is 1 or 2, the time taken for such pipette tip(s) C2 loaded by mistake to pass through the space S3 is momentary. In this case, it is considered as unnecessary to make the user notice that pipette tip(s) C2 have been loaded by mistake, or to stop transfer of cuvettes C1. Therefore, in S208, the number of pipette tips C2 loaded by mistake is reset.

Next, when the value of n is 3 (S209: YES), the CPU 31a performs an abnormality handling process (S210). For example, in such a case where the user loaded by mistake pipette tips C2 of a whole bag into the first hopper 511, the value of n becomes greater than or equal to 3 before the elapsed time T reaches the predetermined value and n is reset. Thus, the abnormality handling process is performed. The abnormality handling process will be described later with reference to FIG. 11. Further, at this time, the CPU 31a lights the indicator 303 in red. When the abnormality handling process is completed, the CPU 31a resumes operations (S211), returns the color of the indicator 303 to the color at normal operation, and then assigns 0 to the value of n. Then, the CPU 31a returns the processing to S202 and continues the processes of S202 to S212 until a shutdown instruction is issued (S213).

Figure 11:
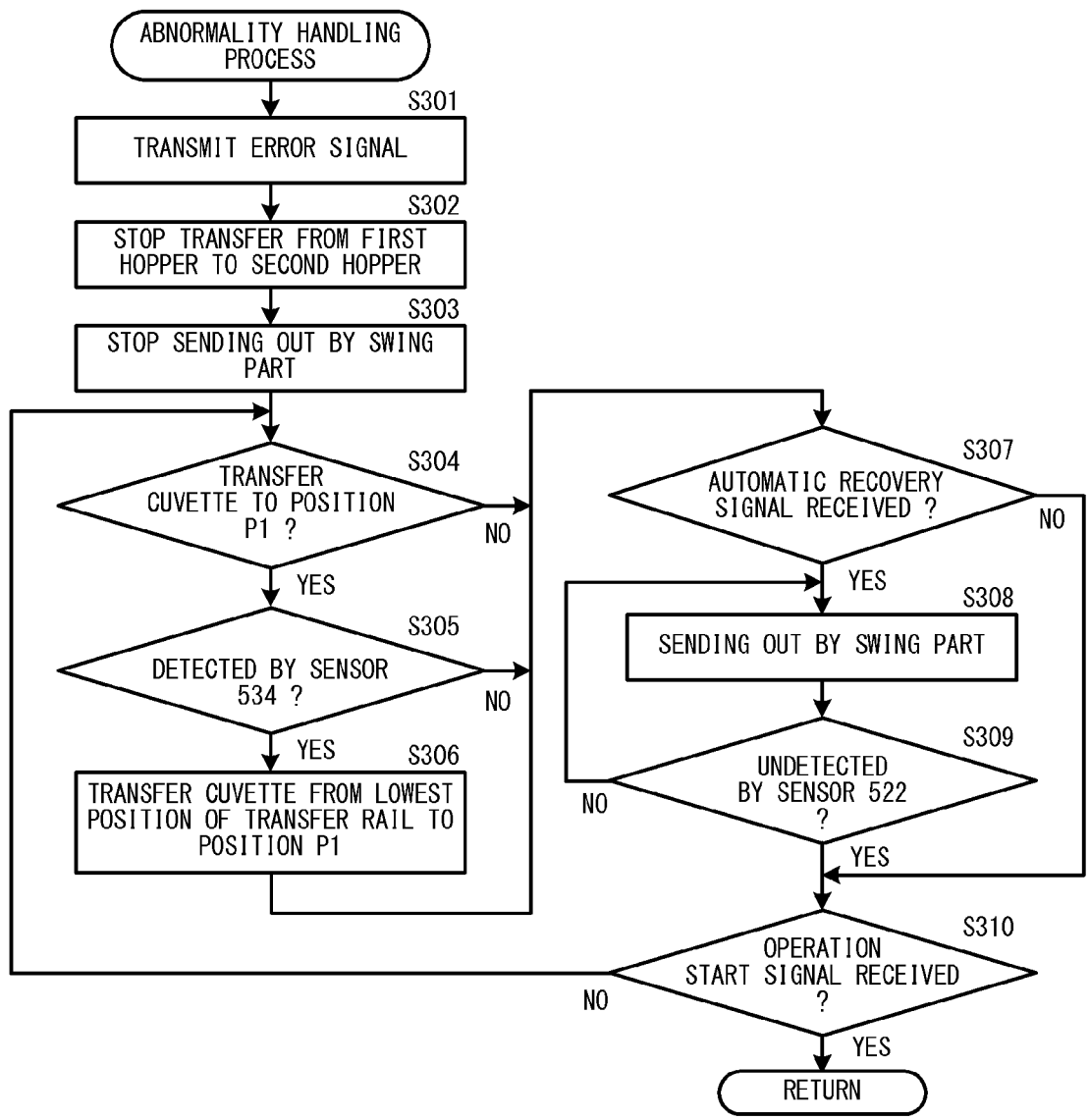
FIG. 11 is a flow chart showing an abnormality handling process according to an embodiment.

FIG. 11 is a flow chart showing the abnormality handling process.

The CPU 31a of the measurement unit 3 transmits an error signal to the control device 4 (S301). Subsequently, by stopping the belt 513, the CPU 31a stops transfer of cuvettes C1 and pipette tips C2 from the first hopper 511 to the second hopper 521 (S302). Moreover, the CPU 31a causes the swing part to stop the sending out, to stop sending out cuvettes C1 and pipettes tip C2 (S303).

Next, the CPU 31a continues only the processes from S101 to S103 in FIG. 9. That is, when it is necessary to transfer a cuvette C1 to the reagent discharging position P1 in order for the R1 reagent to be discharged (S304: YES), the CPU 31a determines whether there is a cuvette C1 at the lowest position P4 of the transfer rails 531 based on a detection signal from the sensor 534 (S305). When there is a cuvette C1 at the lowest position P4 (S305: YES), the CPU 31a causes this cuvette C1 to be transferred to the reagent discharging position P1 (S306). Accordingly, only the cuvettes C1 being held on the transfer rails 531 will be sent to the subsequent stages.

Further, the CPU 31a determines whether it has received an automatic recovery signal from the control device 4 during the abnormality handling process (S307). Upon receiving an automatic recovery signal (S307: YES), the CPU 31a causes the swing part to perform the sending out, to send out a cuvette C1 or a pipette tip C2 on the bottom surface of the second hopper 521 (S308). Then, based on a detection signal form the sensor 522, the CPU 31a determines whether neither a cuvette C1 nor a pipette tip C2 is on the bottom surface of the second hopper 521 (S309). When there are cuvettes C1 or pipette tips C2 on the bottom surface of the second hopper 521 (S309: NO), the processing is returned to S308. As a result, all cuvettes C1 in the second hopper 521 are transferred to the transfer rails 531, and all pipette tips C2 in the second hopper 521 are sent to the space S3.

It should be noted that, when a cuvette C1 is sent out to the transfer rails 531 in S308, cuvettes C1 may be held in the transfer rails 531 exceeding the middle position of the transfer rails 531. However, since only several cuvettes C1 are held in the second hopper 521, all the cuvettes C1 in the second hopper 521 will be transferred to the transfer rails 531.

Further, the CPU 31a determines whether it has received an operation start signal from the control device 4 during the abnormality handling process (S310). Until receiving an operation start signal (S310: YES), the CPU 31 returns the processing to S304 and continues the processes of S304 to S309.

Figure 12A:
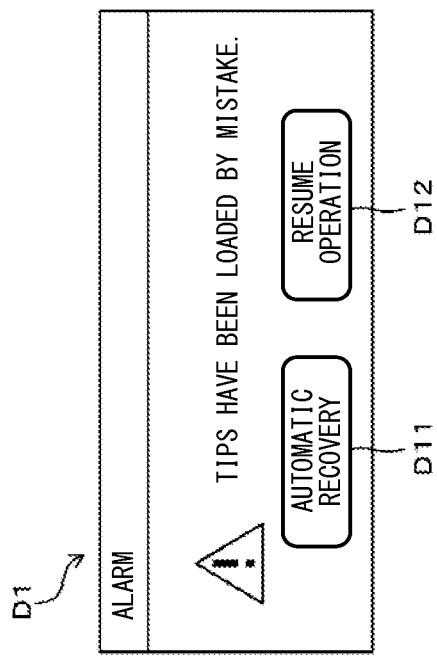
FIG. 12A-FIG. 12B are a flow chart (FIG. 12A) showing processing performed by a control device and a dialogue box (FIG. 12B) according to an embodiment.

FIG. 12A is a flow chart showing processing performed by the control device 4.

The CPU 401 of the control device 4 repeats determining whether it has received an error signal from the measurement unit 3 (S401) until a shutdown instruction is issued (S407: YES). Upon receiving an error signal (S401: YES), the CPU 401 causes the display input unit 41 to display a dialogue D1 including an error message (S402).

Figure 12B:
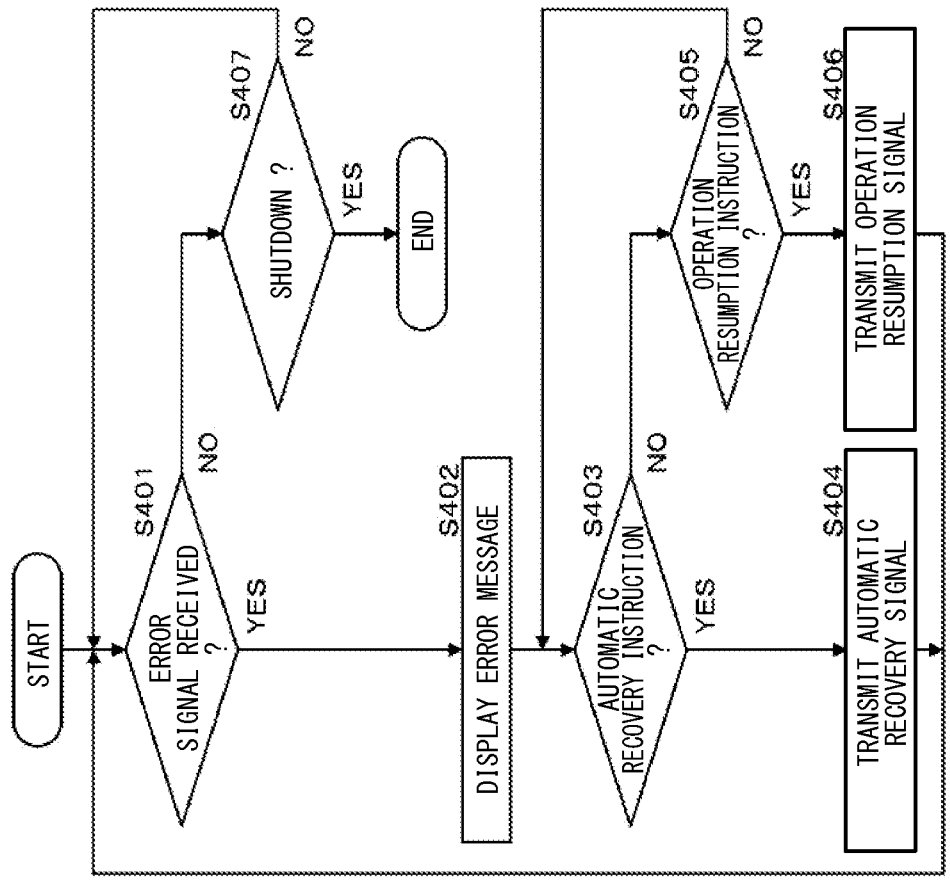

FIG. 12B shows the dialogue D1. In the dialogue D1, an error message indicating that pipette tips C2 were loaded by mistake is displayed. Moreover, the dialogue D1 includes an automatic recovery button D11 and an operation resumption button D12.

With reference back to FIG. 12A, the CPU 401 causes the processing to wait until the automatic recovery button D11 or the operation resumption button D12 is pressed (S403, S405). When the automatic recovery button D11 is pressed (S403: YES), the CPU 401 transmits an automatic recovery signal to the measurement unit 3 (S404), and when the operation resumption button D12 is pressed (S405: YES), the CPU 401 transmits an operation resumption signal to the measurement unit 3 (S406).

As described above, according to the present embodiment, each cuvette C1 loaded into the first hopper 511 through the inlet 511a is transferred to the second hopper 521, and then sent out by the swing part to be transferred onto the transfer rails 531. On the other hand, each pipette tip C2 loaded by mistake into the first hopper 511 is transferred to the second hopper 521, and then sent out by the swing part to be sent into the space S3 through the space S1 only or through the spaces S1 and S2. The pipette tip C2 sent into the space S3 is housed in the storage 380. Accordingly, the user need not perform complicated restoration operations in order to remove the pipette tip C2 loaded by mistake, and can take out the pipette tip C2 loaded by mistake, by removing the pipette tip C2 held in the storage 380.

Further, according to the present embodiment, the diameter d11 of the flange C11 of each cuvette C1 is greater than the intervals d3 and d4 of the spaces S1 and S2, and the diameter d12 of the body C12 of the cuvette C1 is smaller than the intervals d3 and d4 of the spaces S1 and S2. Accordingly, only the flange C11 of the cuvette C1 enters neither the space S1 nor the space S2, and thus, the cuvette C1 is transferred onto the transfer rails 531. Further, the diameter of the pipette tip C2 transferred from the second hopper 521 is smaller than the intervals d3 and d4 of the spaces S1 and S2. Thus, in the present embodiment, cuvettes C1 and pipette tips C2 loaded by mistake can be sorted from each other, through such a simple configuration.

Further, according to the present embodiment, when it is determined that pipette tips C2 have been sent to the space S3 based on detection signals from the sensor 556 provided in the guide part 55, the dialogue D1 indicating that pipette tips C2 were loaded by mistake is displayed on the display input unit 41. Accordingly, the user can promptly notice that pipette tips C2 were loaded into the first hopper 511 by mistake, and thus, can quickly take a subsequent countermeasure (for example, measures of removing the pipette tips C2 and then resuming the operation of the cuvette supplying section 5). Therefore, it is possible to suppress the restoration operation from becoming complicated.

Further, according to the present embodiment, in the abnormality handling process, although transfer from the first hopper 511 to the second hopper 521 and sending out by the swing part are stopped, transfer of the cuvettes C1 on the transfer rails 531 are continued as appropriate, as shown in S304 to S306. Accordingly, different from a case where all transfer operations in the cuvette supplying section 5 are stopped, measurement operation can be continued, using the cuvettes C1 remaining on the transfer rails 531.

Further, according to the present embodiment, since transfer of pipette tips C2 loaded by mistake into the first hopper 511 is automatically stopped. Therefore, the user need not stop such operation manually, and thus the burden on the user is reduced. Further, transfer of the pipette tips C2 loaded by mistake can be promptly stopped.

Further, according to the present embodiment, when the abnormality handling process is started, the dialogue D1 shown in FIG. 11B is displayed. Accordingly, the user can quickly stop the immune analyzer 1 and quickly take a countermeasure such as removing the pipette tips C2.

Further, according to the present embodiment, each pipette tip C2 sent into the space S3 is guided by the plates 551 to 553 and the walls 554 and 555 which form the space S3, to the disposal channel which continues to the storage 380. In the present embodiment, through a simple configuration using the weight of the pipette tip C2 itself as described above, the pipette tip C2 loaded by mistake can be easily guided to the storage 380.

Further, according to the present embodiment, the storage 380 set inside the measurement unit 3 is configured to be able to be taken outside when the door 302 is opened. Accordingly, simply by opening the door 302 and taking out the storage 380, the user can easily remove pipette tips C2 loaded by mistake.

Further, according to the present embodiment, cuvettes C1 are each transferred with the flange C11 supported by the upper sides of the pair of plates 523a and the pair of transfer rails 531. Pipette tips C2 pass through the space S1 formed by the pair of plates 523a and the space S2 formed by the pair of transfer rails 531, and are sent to the space S3. In this manner, since pipette tips C2 are sorted by using the plates 523a and the transfer rails 531 for transferring cuvettes C1, the measurement unit 3 can be configured in a simple manner, without separately using an apparatus for sorting cuvettes C1 and pipette tips C2.

Further, according to the present embodiment, as shown in FIG. 2A, the first hopper 511 for loading cuvettes C1 and the hopper 611 for loading pipette tips C2 are adjacent to each other. Therefore, cuvettes C1 and pipette tips C2 can be easily refilled. That is, according to the present embodiment, in specimen analyzing processing, cuvettes C1 and pipette tips C2 are consumed by the same number. Therefore, it becomes necessary to refill cuvettes C1 and pipette tips C2 into the first hopper 511 and the hopper 611, respectively, at substantially the same time. Therefore, by making the first hopper 511 and the hopper 611 adjacent to each other, cuvettes C1 and pipette tips C2 can be refilled into the first hopper 511 and the hopper 611, through a series of operations.

However, when the first hopper 511 and the hopper 611 are adjacent to each other in this manner, loading pipette tips C2 by mistake into the first hopper 511 is more likely to occur. As described above, since cuvettes C1 and pipette tips C2 are refilled into the first hopper 511 and the hopper 611 often through a series of operations, if the first hopper 511 and the hopper 611 are adjacent to each other, loading pipette tips C2 by mistake into the first hopper 511 is more likely to occur.

However, even in a case where loading pipette tips C2 by mistake is likely to occur, according to the present embodiment, the pipette tips C2 loaded by mistake are removed from the path for transferring cuvettes C1, and sent to the storage 380. At the same time, occurrence of the loading by mistake is indicated, and the user is notified thereof. Therefore, if the loading by mistake should occur, the user can smoothly take measures after occurrence of such loading by mistake. Thus, in the present embodiment, by arranging the first hopper 511 and the hopper 611 so as to be adjacent to each other, convenience for the user is improved, and at the same time, even if loading by mistake should occur, the user can easily take measures thereafter.

Although an embodiment of the present invention has been described, the embodiment of the present invention is not limited thereto.

For example, in the above embodiment, an example has been shown in which blood is measured. However, urine may be measured. That is, the present invention can be applied to analyzers that test urine, and further, the present invention can be applied to clinical sample testing apparatus that test other clinical samples.

In the above embodiment, the cuvette C1 and the pipette tip C2 are sorted from each other. However, the present invention is not limited thereto. The cuvette C1 and a cuvette used in another apparatus (such as blood coagulation apparatus) that is different from the immune analyzer 1 may be sorted from each other. In this case, it is sufficient that the diameter of the cuvette for said another apparatus to be sorted is smaller than the diameter d11 of the cuvette C1.

In the above embodiment, the cuvette C1 and the pipette tip C2 are sorted from each other based on the difference in the shape of the cuvette C1 and the pipette tip C2. However, the present invention is not limited thereto. Two types of articles may be sorted, based on the articles having similar shapes but different sizes. For example, in a case where the cuvette C1 and a cuvette used in another apparatus are sorted from each other, the outer shape of the cuvette used in said another apparatus and the outer shape of the cuvette C1 may be in a similarity relationship with each other but have sizes different from each other. That is, "having a shape different" in claims includes "having a similar figure but a different size".

In the above embodiment, the cuvette C1 and the pipette tip C2 are sorted from each other by means of the space S1 formed by the plates 523a and the space S2 formed by the transfer rails 531. However, the present invention is not limited thereto. A configuration for sorting the cuvette C1 and the pipette tip C2 from each other may be provided in the first hopper 511 or the second hopper 521. For example, a plurality of elongated openings are formed in the first hopper 511 or the second hopper 521, and the gap in each opening is set to have dimensions that allow the pipette tip C2 to pass therethrough but does not allow any portion of the cuvette C1 pass therethrough. Further, a guide part is provided that guides pipette tips C2 having passed through such openings to the storage 380. Alternatively, a configuration for sorting the cuvette C1 and the pipette tip C2 from each other may be provided at a position different from the cuvette supplying section 5. For example, an opening may be provided at the reagent discharging position P1 at which a cuvette C1 is supplied by the cuvette supplying section 5. Then, the opening may be set to have dimensions that allow the pipette tip C2 to pass therethrough but cause the flange C11 of the cuvette C1 to be supported by the edges of the opening.

In the above embodiment, the cuvette C1 and the pipette tip C2 are sorted from each other through the spaces S1 and S2. However, the present invention is not limited thereto. Such sorting may be performed by another sorting configuration. For example, into an opening whose diameter is greater than d21 and smaller than d12, cuvettes C1 and pipette tips C2 are sent from above. Then, the cuvettes C1 which do not pass through this opening may be supplied to the mechanisms of the subsequent stages, and the pipette tips C2 which have passed through this opening may be housed in the storage 380.

That is, in the above embodiment, as shown in FIG. 5B, by arranging the pair of plates 523a so as to face each other, a gap (the space S1) for sorting the cuvette C1 and the pipette tip C2 from each other is formed. Also, as shown in FIG. 5C, by arranging the pair of transfer rails 531 so as to face each other, a gap (the space S2) for sorting the cuvette C1 and the pipette tip C2 from each other is formed. However, the method for forming a gap for sorting the cuvette C1 and the pipette tip C2 from each other is not limited thereto. These gaps may be formed by openings, cutouts, or the like. That is, the "gap" described in claims also include a gap formed by such an opening, a cutout, or the like.

Further, the cuvette C1 and the pipette tip C2 are sorted from each other based on the difference in their shapes in the above embodiment. However, in a case where the cuvette C1 and the pipette tip C2 are different from each other both in their shapes and their weights, the cuvette C1 and the pipette tip C2 may be sorted from each other based on their weights. In this case, for example, by arranging on the path for transferring the cuvette C1 a receiving part that descends if the weight of an article placed thereon exceeds a predetermined weight, the cuvette C1 and the pipette tip C2 may be sorted from each other.

In the above embodiment, by only pipette tips C2 loaded by mistake being sent to the space S3, cuvettes C1 are supplied to the mechanisms of the subsequent stages. However, the present invention is not limited thereto. It may be configured such that consumables sent to the space S3 are supplied to the mechanisms of the subsequent stages, and consumables sent onto the transfer rails 531 are discarded. In this case, the storage 380 is provided at the end of the transfer rails 531, and a mechanism for sending the consumables to the mechanisms of the subsequent stages is provided at the end of the space S3.

In the above embodiment, each pipette tip C2 is removed through the space S1 formed by the plates 523a and the space S2 formed by the transfer rails 531. However, the present invention is not limited thereto. The pipette tip C2 may be removed only through the space S1. In this case, for example, by the swing part slowly performing the sending out operation, the pipette tip C2 may be prevented from entering the space S2. Further, by locating the stopper 532a of the cover 532 at the highest position of the transfer rails 531, the pipette tip C2 may be prevented from entering the space S2.

Figure 13A:
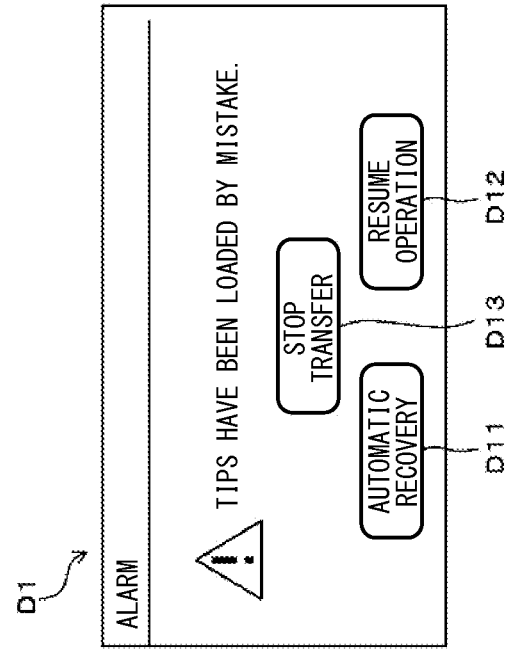
FIGS. 13A-13B are a disposal box (FIG. 13A) set outside and a dialogue box (FIG. 13B) according to a modification.

In the above embodiment, the space S3 is connected to the disposal channel which continues to the storage 380, and the pipette tips C2 sent to the space S3 are housed in the storage 380. However, the present invention is not limited thereto. As shown in FIG. 13A, it may be configured such that the space S3 is connected to a disposal tube 305 which is led to the outside of the measurement unit 3, and the pipette tips C2 sent into the space S3 pass through the disposal tube 305 to be housed in a disposal box set outside the measurement unit 3.

Figure 13B:
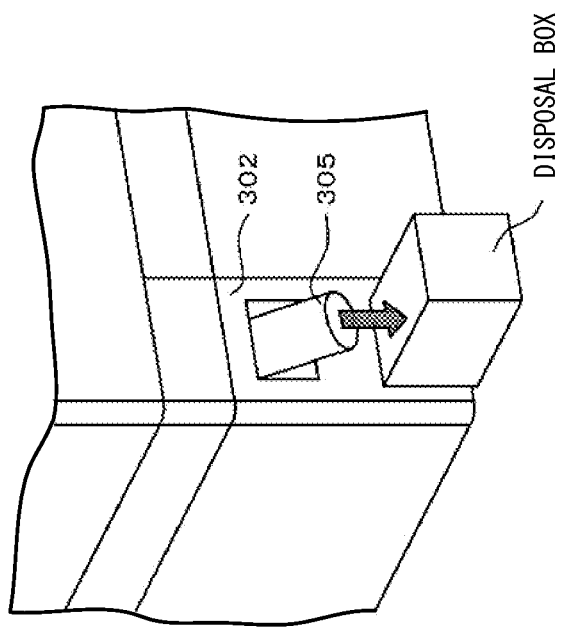

Further, in the above embodiment, when the abnormality handling process is started, transfer from the first hopper 511 to the second hopper 521 and sending out by the swing part are automatically stopped. However, such transfer and sending out may not be automatically stopped. In this case, as shown in FIG. 13B, it may be configured such that a transfer stop button D13 for stopping the above transfer and sending out is provided in the dialogue D1 for making notification of pipette tips C2 having been loaded by mistake. Then, when the transfer stop button D13 is pressed, the above transfer and sending out are stopped. In such a configuration, when the user notices that pipette tips C2 have been loaded by mistake, the user can promptly stop the above transfer and sending out. In addition, since the user need not press the emergency stop button 304b (see FIG. 1), the user can stop only the above transfer and sending out, without stopping all the operations performed in the measurement unit 3.

In the above embodiment, when the abnormality handling process is started, the dialogue D1 is displayed in the display input unit 41, and the indicator 303 is lit in red. However, the present invention is not limited thereto. An alarm sound for notifying the user an abnormality may be outputted from a speaker provided in the measurement unit 3 or the control device 4.

In the above embodiment, when the elapsed time T has become longer than or equal to a predetermined value (e.g., 3 minutes) since a pipette tip C2 sent to the space S3 was detected for the first time, the value of n is returned to 0. However, the value of n may not be returned to 0. Alternatively, when the driven number of the swing part has become greater than or equal to a predetermined value since a pipette tip C2 sent to the space S3 was detected for the first time, the value of n may be returned to 0. Still alternatively, these predetermined values may be freely set by the user.

In addition to the above, various modifications of the embodiment of the present invention can be made as appropriate without departing from the scope of the technical idea defined by the claims.

What is claimed is:

1. A specimen analyzer comprising:
   a measurement mechanism section configured to measure a specimen by using a cuvette and a pipette tip having a diameter smaller than that of the cuvette;
   a cuvette reservoir configured to accommodate a plurality of cuvettes and having an inlet for loading the plurality of cuvettes;
   a supplying section configured to supply the cuvette accommodated in the cuvette reservoir, to the measurement mechanism section;
   the supplying section further comprising a sorter connected to the cuvette reservoir and including a gap configured to allow the pipette tip to pass therethrough but not allow the cuvette to pass therethrough;
   the supplying section further comprises a pair of transfer rails configured to engage the cuvette and to transfer cuvettes one by one, and a space between the pair of transfer rails is configured to allow the pipette tip to fall down but not to allow the cuvette to fall down; and
   a storage below the supplying section configured to house the pipette tip which has passed through the gap.

2. The specimen analyzer of claim 1, further comprising:
   a guide part configured to guide, to the storage, the pipette tip which has passed through the gap.

3. The specimen analyzer of claim 2, wherein
the guide part is further configured to guide, to the storage, the pipette tip which has passed through the space, by causing the pipette tip to fall down along the guide part from the space to the storage.

4. The specimen analyzer of claim 1, wherein
the measurement mechanism section comprises a specimen dispensing mechanism configured to dispense the specimen in the cuvette and including a dispensing nozzle, and a detector configured to measure an object in the specimen,
wherein the pipette tip is configured to be attached to a tip of the dispensing nozzle.

5. The specimen analyzer of claim 1, further comprising:
a pipette tip reservoir configured to accommodate a plurality of pipette tips and having a second inlet for loading the plurality of pipette tips.

6. The specimen analyzer of claim 5, wherein
the inlet of the cuvette reservoir and the second inlet of the pipette tip reservoir are arranged so as to be adjacent to each other.

7. The specimen analyzer of claim 1, wherein
the cuvette and the pipette tip are tubular; and
the space between the pair of transfer rails is smaller than a maximum diameter of the cuvette and is greater than a maximum diameter of the pipette tip.

8. The specimen analyzer of claim 1, wherein
the cuvette and the pipette tip are tubular;
the sorter is configured to transfer the cuvette and cause the pipette tip to fall down, and
a guide part is configured to guide, to the storage, the pipette tip that has fallen down from the gap.

9. The specimen analyzer of claim 1, further comprising:
a sensor configured to detect the pipette tip which has passed through the gap.

10. The specimen analyzer of claim 1, wherein
the storage is set within an inner area of the specimen analyzer, and is configured to be able to be taken outside the specimen analyzer.

11. A specimen analyzer comprising:
a cuvette reservoir configured to accommodate a plurality of cuvettes and having a first inlet for loading the plurality of cuvettes;
a pipette tip reservoir configured to accommodate a plurality of pipette tips and having a second inlet for loading the plurality of pipette tips;
a measurement mechanism section comprising a specimen dispenser configured to dispense a specimen in the cuvette supplied from the cuvette reservoir and including a dispensing nozzle, a reagent dispenser configured to dispense a reagent in the cuvette and a detector configured to measure an object in the specimen, wherein the pipette tip supplied from the pipette tip reservoir is configured to be attached to a tip of the dispensing nozzle;
a supplying section configured to supply the cuvette accommodated in the cuvette reservoir, to the measurement mechanism section;
the supplying section comprises a pair of transfer rails configured to engage the cuvette and to transfer cuvettes one by one, and a space between the pair of transfer rails is configured to allow the pipette tip to fall down but not to allow the cuvette to fall down;
the supplying section further comprises a sorter connected to the cuvette reservoir and comprising a gap configured to allow the pipette tip to pass therethrough but not to allow the cuvette to pass therethrough; and
a storage below the supplying section configured to house the pipette tip which has passed through the gap.

12. The specimen analyzer of claim 11, further comprising a guide part configured to guide, to the storage, the pipette tip which has passed through the gap, by causing the pipette tip to fall down along the guide part from the gap to the storage.

* * * * *